United States Patent [19]

Fischer

[11] 3,986,499

[45] Oct. 19, 1976

[54] ORTHOPEDIC EXTENSION APPARATUS

[76] Inventor: Hans W. R. Fischer, Chemin de la Metairie, CH-1218 Grand-Saconnex, Switzerland

[22] Filed: May 21, 1975

[21] Appl. No.: 579,459

[30] Foreign Application Priority Data

May 24, 1974 Germany ........................... 2425295

[52] U.S. Cl. .................................................. 128/71

[51] Int. Cl.² ........................................... A61F 5/00

[58] Field of Search .................... 128/71, 68, 75, 24

[56] References Cited

UNITED STATES PATENTS

| | | | |
|---|---|---|---|
| 902,946 | 11/1908 | DeNise | 128/71 UX |
| 1,628,369 | 5/1927 | McBurney | 128/71 |
| 2,511,061 | 6/1950 | Hughes | 128/71 UX |
| 2,798,481 | 7/1957 | Matthews | 128/71 |
| 3,354,879 | 11/1967 | Briggs | 128/71 |

FOREIGN PATENTS OR APPLICATIONS

| | | | |
|---|---|---|---|
| 1,187,011 | 4/1970 | United Kingdom | 128/71 |

*Primary Examiner*—Lawrence W. Trapp
*Attorney, Agent, or Firm*—Smythe & Moore

[57] ABSTRACT

Orthopedic extension apparatus having a lower part and a swingable carrier pivotally mounted thereon, spaced fastening means for holding the patient at spaced parts to which tension is to be applied, the carrier being connected to a fastening means at a point spaced from the pivot, the carrier receiving the legs of the patient which can exert force thereon to apply tension between the spaced fastening means.

16 Claims, 8 Drawing Figures

ORTHOPEDIC EXTENSION APPARATUS

The present invention relates to an orthopedic extension apparatus with two fasteners for the body, the distance apart of which can be increased in order to treat complaints of the spinal column, and having a support for the supporting of the lower legs of the person being treated.

Orthopedic extension apparatus of the aforementioned type serve to relieve the spinal column of the person treated from pressure by producing a relaxation of the muscles of the spinal column. This desired relaxation of the muscles is obtained by exerting on the cramped muscles forces of extension which lead to reduction of the muscle tension.

One extension apparatus of the type in question is known which is formed of a table consisting of two parts with one part being attached to the head or chest of the patient and the other part strapped to the abdominal area, with the two parts capable of being moved away from each other by a hydraulic system after the patient has assumed the position for treatment. Such a known extension apparatus is not fully satisfactory since it is of complicated construction, is expensive, and does not permit operation by the patient himself. Furthermore, it is not suitable for use on a sickbed.

The object of the present invention is to provide an extension apparatus of the above indicated type which is of very simple construction and is easy to operate.

This goal is achieved in accordance with the invention in the manner that the extension apparatus has a bottom part as well as a carrier for a support which is swingably supported on said bottom part and one holding device is fastened to the lower part while the other one is connected with the carrier at a distance from the axis of rotation of the latter.

The extension apparatus of the invention affords the advantage that the patient himself applies the force necessary for the extension in the manner that by pushing against the support with his lower legs he introduces into the carrier a moment of rotation which is transmitted to the fastener attached to the carrier and is used for the stretching. Overstraining of the muscles is definitely avoided with the apparatus of the invention without complicated control devices being required for this.

It has been found particularly advantageous to develop the lower part of the extension apparatus in the form of a frame. By this frame-like construction of the lower part the possibility is provided of using the extension apparatus in the bed of the patient. The patient therefore need no longer stand up after the treatment but can remain lying and then, for instance, commence his nightly sleep immediately after the treatment.

The swinging movements of the carrier of the extension apparatus can preferably be limited by a stop which should be adjustable. The stop can be formed by a rope which connects the carrier to the frame. Instead of a rope a stop in the swivel bearing of the carrier could also be employed.

In view of the comparatively large extension forces which can be produced, it is important to use comfortable fasteners for the body which do not result in any pain. In particular, the clamping forces which are directed substantially radially to the center of the body by fasteners for the lower part of the body must be as small as possible without thereby causing an unintended displacement of the strap. This is achieved in the case of a fastener formed of an abdominal belt in which the abdominal belt is connected on both sides by straps with the extension apparatus in the manner that the abdominal belt is provided with diagonally extending pull strands to which the belts are connected and by which the forces acting in the belts on in each case one side of the abdominal belt can be transmitted to the other side of the abdominal belt.

As fastener for the upper part of the body there are advisedly used lengths of strap which are connected with a central part which has a supporting part which forms a bead-like abutment, the upper limiting line of which has a ridge shape, which is adapted to the human costal arch.

The invention will be explained in further detail below with reference to the accompanying drawings in which.

Figure 1:
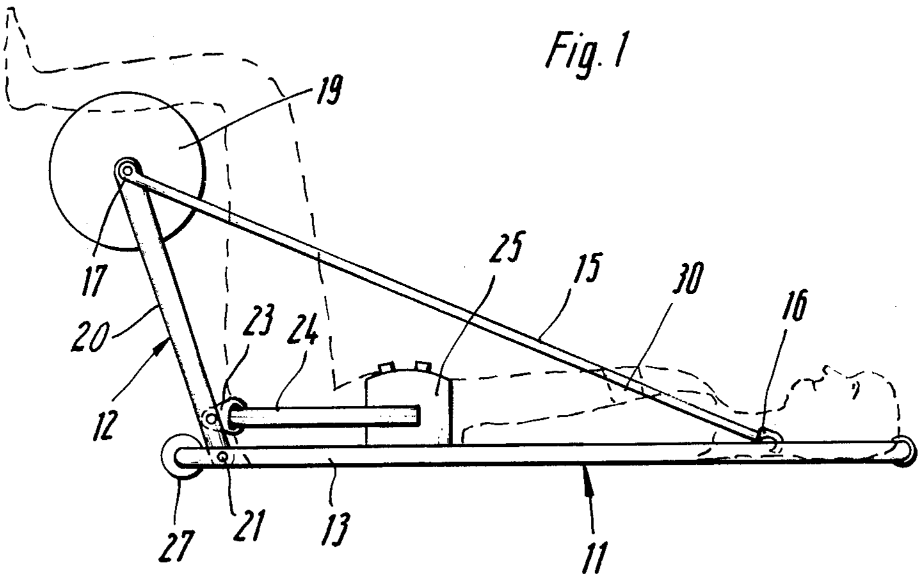
FIG. 1 is a side view of an extension apparatus in accordance with the invention.

In the Figures, 11 is the bottom part of an extension apparatus and 12 is the carrier which is swingably supported on the lower part 11. The lower part 11 is formed of a tubular frame which, in order to reduce its weight, consists of light metal. The longitudinal members 13 of the frame are provided with holes 14 into which hooks 16 arranged at the end of a rope 15 can be introduced. The ends of the ropes 15 opposite the hooks 16 wrap around pins 17 which are formed by the extensions of a shaft 18 on which a support 19, which is preferably cushioned and developed as a roller, is supported. The shaft 18 is held by the longitudinal members 20 of the U-shaped carrier 12.

On the end of the longitudinal members 20 of the carrier 12 which face away from the shaft 18, the carrier 12 is supported for turning around an axis 22 by means of pins 21. At a distance from the pivot axis 22 there are arranged on each longitudinal member 20 of the carrier 12 swingably arranged fittings 23 the distance of which from the swivel axis 22 is variable and which serve for fastening two, preferably adjustable straps 24, which together with an abdominal belt 25 form a fastener for the lower body of a person to be treated.

The transverse member 26 of the lower part 11 bears two rollers 27 which facilitate the moving of the extension apparatus. On the transverse member 28 of the lower part there are arranged two buckles 29 for the applying of a strap forming a second fastener 30.

When using the extension apparatus described, the patient rests his back in the region of the lower part 11 defined by the longitudinal members 13 and the transverse members 26 and 28, or the frame forming the lower part 11 is placed over a patient as he is lying in bed, his lower legs being placed on the support 19. By means of the fastener 30 he secures the starting position of the upper body or the head and by means of the fastener 24, 25 he secures the starting position of the hips. In this starting position the ropes 15 are relaxed and the carrier is substantially vertical so that no disturbing forces occur upon the application of the fasteners. Due to the weight exerted by the lower legs on the support 19 a counterclockwise rotational movement is thereupon exerted on the carrier 12, the amount of which depends on the size and direction of the force applied, the length of the longitudinal members 20 and their angular position. By means of the fittings 23 a stretching force proportional to the moment of rotation introduced into the carrier 12 is exerted on the strap 24 and the abdominal belt 25. The amount of the extension is limited by the ropes 15, the hooks 16 of which are introduced into a pair of holes 14. After stretching, the patient can himself loosen the fasteners, lift the transverse member 28 and push the entire apparatus, for instance, away from his bed by means of the rollers 27.

Of course, it is also possible, instead of using the ropes 15 for limiting the swinging motion of the carrier 12, to employ other stops which can be arranged, for instance, in the vicinity of the pins 21.

Figure 2:
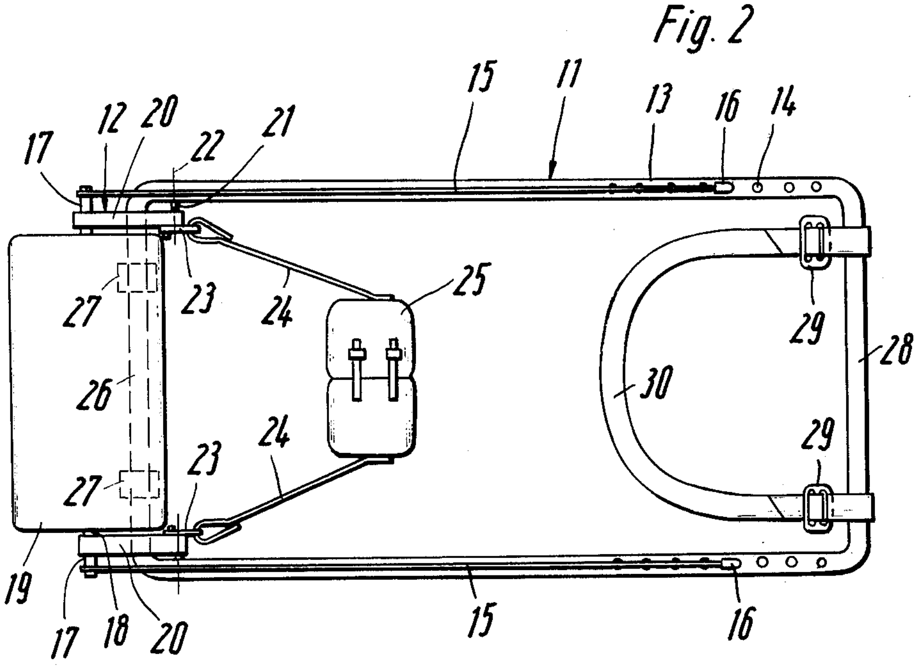
FIG. 2 is a top view of the extension apparatus shown in FIG. 1.
Figure 3:
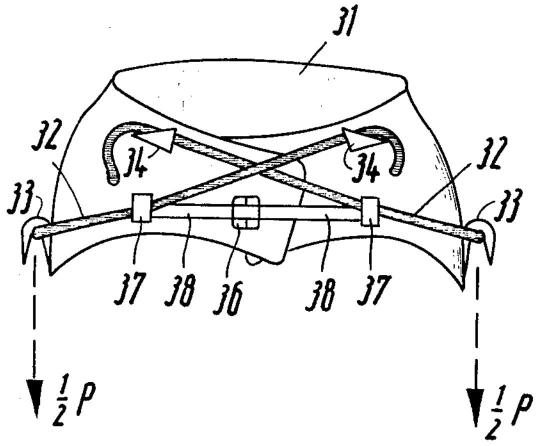
FIG. 3 is a front view of an abdominal belt for a fastener for the lower body of a patient to be treated with the extension apparatus shown in FIGS. 1 and 2.
Figure 4:
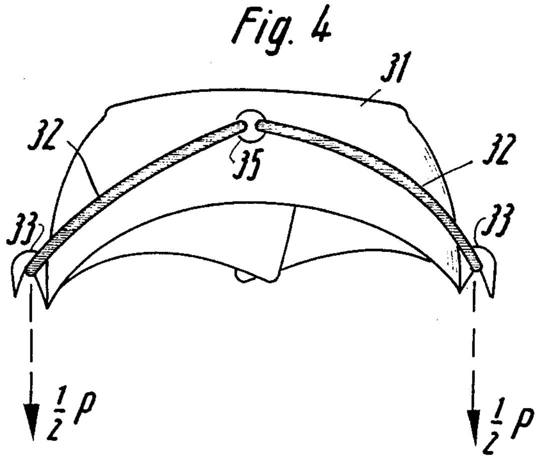
FIG. 4 is a rear view of the abdominal belt of FIG. 3.

In FIGS. 3 and 4, 31 is a wide abdominal belt of sufficiently strong flexible material. Around the abdominal belt 31 there extend diagonally two pull strands 32 developed as prestretched plastic cords. Displaceable fastening elements 33 are arranged on the pull strands and can be connected to straps which correspond to the straps 24 in FIGS. 1 and 2. Each of the fastening elements 33 transmits half the force of extension P to the pull strands 32, the latter are held on the front side of the abdominal belt 31 in detachable manner by clamps 34 and at the rear of the abdominal belt in nondetachable manner by an anchoring member 35. The clasp 36 serves to connect together two short bands 38 having at their ends passage loops 37 for the pull strands 32 after the strap has been placed around the body of the patient.

By the design selected, assurance is had that the forces of extension are transmitted to the abdominal belt 31 in such a manner that they themselves produce the tensioning forces which act radially inwards on the body and hold the abdominal belt fast. These tensioning forces are accordingly proportional to the forces of extension and occur only simultaneously with the latter. This is far more pleasant for the patient than the lashing tight of the abdominal belt independent of the force of extension before the actual extending.

Figure 5:
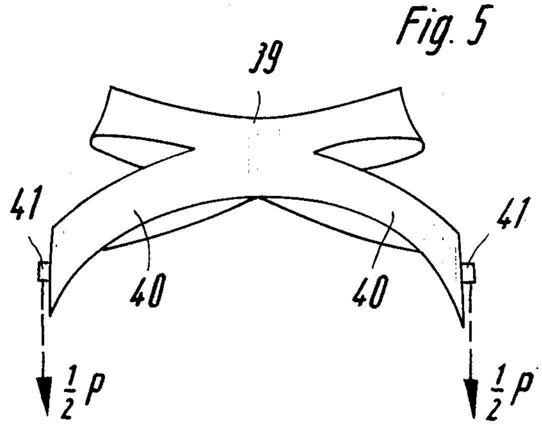
FIG. 5 is a rear view of an abdominal belt of a modified construction.

The use of pull strands 32 in the form of cords has the advantage that the cords can slide over the outer surface of the belt when they transmit the force exerted on them to the other side of the abdominal belt 31. A simplified embodiment, which does not afford this advantage, is shown in FIG. 5. It shows an abdominal belt 39 in connection with which the pull strands 40 are formed of parts of the abdominal belt itself. The position of the fastening elements 41 in this embodiment cannot be changed with respect to the pull strands 40 which, when an extension force is applied, consequently carry out a certain movement relative to the body.

Figure 7:
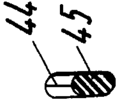
FIG. 7 is a cross section along the line VII—VII of FIG. 6.
Figure 6:
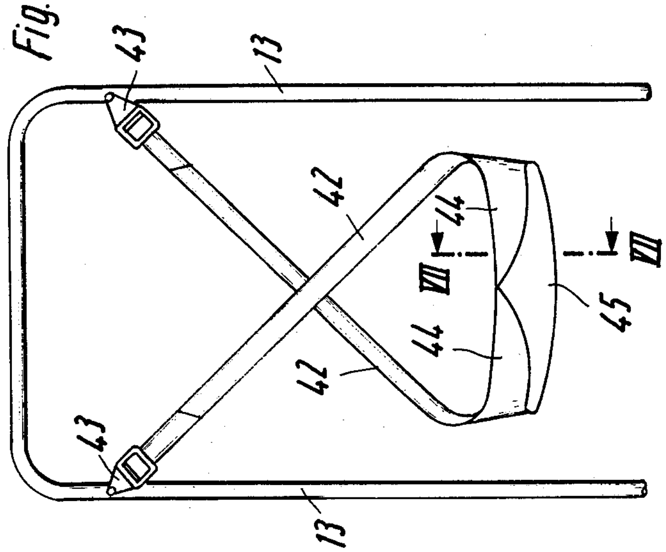
FIG. 6 shows a fastener for the upper part of the body of a patient.

In FIG. 6, 42 are two strap sections fastened by means of buckles 43 to the longitudinal members 13 of an extension apparatus, said sections widening to form a central portion 44 which bears a substantially triangular supporting part 45 forming a bead-like abutment (see FIG. 7), whose upper limiting line has a ridge shape which is adapted to the costal arch of the patient. By the proposed development of the supporting part the extension forces can be introduced into the upper body of the patient over the chest in a manner which is particularly pleasant.

Figure 8:
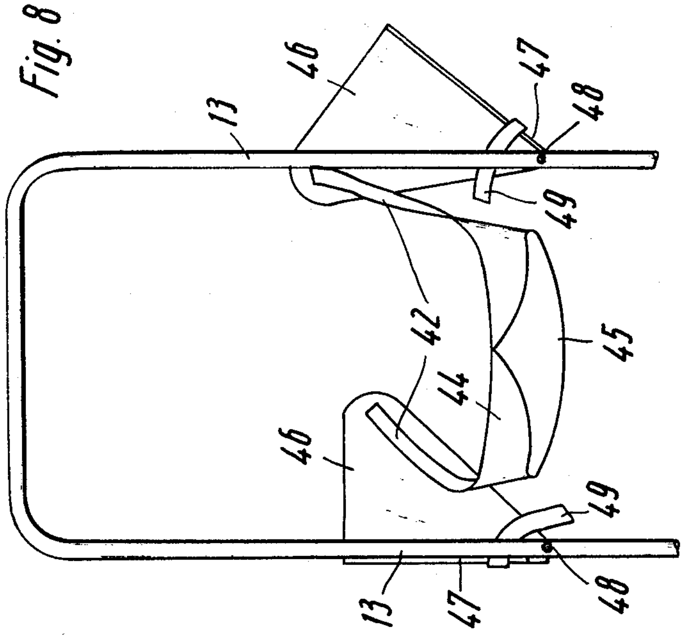
FIG. 8 shows another fastener for the upper part of the body.

Finally, FIG. 8 shows a particularly advantageous manner of fastening the strap sections 42 to the longitudinal members 13 of an extension apparatus. Flat swingable extensions 46 are employed having stop fillets 47. On these extensions 46 which can be swung on the pin 48 there are provided slits for the strap sections 42 whose ends 49 are automatically clamped fast in the operating position shown on the left-hand side of FIG. 8 between the stop fillets 47 and the longitudinal members 13.

What is claimed is:

1. Orthopedic extension apparatus comprising a frame for generally horizontally supporting the body of a person being treated, said frame including spaced foot, abdominal and upper body sections, spaced body engaging means arranged on said frame and respectively pivotally connected by fastening means to said foot section and the opposing upper end of said body section for engaging with the abdominal and upper body areas of the body, said foot section being pivoted at its lower end to the frame for swinging movement and being inclined upwardly and forwardly relative thereto, support means on the upper end of said foot section over which the shanks of the bent legs of the body extend and are supported thereby, fastening means pivotally connected to the upper end of said foot section and extending rearwardly and pivotally connected to the upper body section of said frame, whereby the person being treated may generate extension traction forces by pushing against said support means with the legs.

2. Extension apparatus according to claim 1, characterized by the fact that the foot section is developed as a U-shaped element.

3. Extension apparatus according to claim 1, characterized by the fact that the swinging motion of the foot section on the pivot axis is limited by fastening means.

4. Extension apparatus according to claim 3, characterized by the fact that the fastening means is adjustable.

5. Extension apparatus according to claim 3, characterized by the fact that the fastening means is formed by a rope which connects the foot section with the frame.

6. Extension apparatus according to claim 1, characterized by the fact that the support means is a roller which is rotatably supported on the carrier.

7. Extension apparatus according to claim 1, characterized by the fact that the frame is provided with casters.

8. Extension apparatus according to claim 1, characterized by the fact that the frame and the foot section consist of light metal tubing.

9. Extension apparatus according to claim 1, characterized by the fact that the distance of the point of attachment of the fastening means which is fastened to the foot section from the pivot axis of the foot section to the frame is variable.

10. Extension apparatus according to claim 1 having a body engaging means formed of an abdominal belt in which the abdominal belt is connected on its two sides with the foot section by straps, characterized by the fact that the abdominal belt is provided with diagonally extending pull strands to which straps are connected and by which the forces acting in the straps in each case on one side of the abdominal belt can be transmitted to the other side of the abdominal belt.

11. Extension apparatus according to claim 10, characterized by the fact that said pull strands are formed of cords which at least partially surround the abdominal belt.

12. Extension apparatus according to claim 10, characterized by the fact that one end of the pull strands is detachably connected to the abdominal belt by clamps.

13. Extension apparatus according to claim 1, characterized by the fact that it has a fastening means with strap sections which are connected with a middle part which has a supporting part which forms a bead-like abutment, the upper limiting line of which has a ridge shape adapted to the human costal arch.

14. Extension apparatus according to claim 13, characterized by the fact that the strap sections are connected with the foot section by means of swingable fastening means.

15. Extension apparatus according to claim 1, characterized by the fact that the foot section is a U-shaped element, the swinging motion of the foot section on the pivot axis is limited by a rope stop and the support means is a roller.

16. Extension apparatus according to claim 1, characterized by the fact that the point of attachment of the fastening means which is fastened to the foot section is variable.

* * * * *